(12) United States Patent
Gao et al.

(10) Patent No.: US 10,260,110 B2
(45) Date of Patent: Apr. 16, 2019

(54) ARTIFICIAL EXOGENOUS REFERENCE MOLECULE FOR TYPE AND ABUNDANCE COMPARISON AMONG DIFFERENT SPECIES OF MICROORGANISMS

(71) Applicant: THE FIRST HOSPITAL OF CHINA MEDICAL UNIVERSITY, Shenyang, Liaoning (CN)

(72) Inventors: Xinghua Gao, Liaoning (CN); Ruiqun Qi, Liaoning (CN); Yuxiao Hong, Liaoning (CN); Hanghang Jiang, Liaoning (CN); Hongduo Chen, Liaoning (CN)

(73) Assignee: THE FIRST HOSPITAL OF CHINA MEDICAL UNIVERSITY, Shenyang, Liaoning (CN)

( * ) Notice: Subject to any disclaimer, the term of this patent is extended or adjusted under 35 U.S.C. 154(b) by 0 days.

(21) Appl. No.: 15/123,931

(22) PCT Filed: Aug. 20, 2015

(86) PCT No.: PCT/CN2015/087624
§ 371 (c)(1),
(2) Date: Sep. 6, 2016

(87) PCT Pub. No.: WO2016/119448
PCT Pub. Date: Aug. 4, 2016

(65) Prior Publication Data
US 2017/0152574 A1 Jun. 1, 2017

(30) Foreign Application Priority Data

Jan. 28, 2015 (CN) .......................... 2015 1 00405500

(51) Int. Cl.
*C12Q 1/6888* (2018.01)
*C12Q 1/686* (2018.01)
*C12Q 1/689* (2018.01)

(52) U.S. Cl.
CPC .......... *C12Q 1/6888* (2013.01); *C12Q 1/686* (2013.01); *C12Q 1/689* (2013.01)

(58) Field of Classification Search
None
See application file for complete search history.

(56) References Cited

U.S. PATENT DOCUMENTS 5,770,360 A * 6/1998 Kievits ................ C12Q 1/6865
435/4
6,312,929 B1 * 11/2001 McMillan .............. C07K 14/78
435/5

(Continued)

OTHER PUBLICATIONS

Charrel et al. BMC Microbiology. 2004. 4:21: 11 pages.*
Hoofar et al. J. Clin. Microbiol. 2004. 42:1863-1868. (Year: 2004).*

*Primary Examiner* — Joseph G. Dauner
(74) *Attorney, Agent, or Firm* — Houtteman Law LLC

(57) ABSTRACT

The present invention provides an artificial exogenous reference molecule for type and abundance comparison among different species of microorganisms. The artificial exogenous reference molecule includes several species detection regions and several linker sequence regions, where the species detection regions and the linker sequence regions are arranged alternately; at least two species detection regions are provided and are species detection regions for different species; and the linker sequence regions are random sequences different from species sequences to be detected. The species detection region includes a primer sequence region and a specific recognition region; the sequence length of the specific recognition region simulates the characteristic detection sequence length of the corresponding species to be (Continued)

detected; and the sequence of the specific recognition region has obviously specific difference from the DNA sequence of a genome in the species to be detected without homology. The artificial exogenous reference molecule provided by the present invention may simultaneously contain universal primer sequence regions of two or more different microorganisms, also contains an artificially recognizable specific sequence, and is used for type and abundance comparison among different species of microorganisms.

6 Claims, 4 Drawing Sheets

Specification includes a Sequence Listing.

(56) References Cited

U.S. PATENT DOCUMENTS

| | | | |
|---|---|---|---|
| 2001/0006800 A1* | 7/2001 | Walkerpeach | C12Q 1/6851 435/91.1 |
| 2004/0072148 A1* | 4/2004 | Ji | C12Q 1/1703 435/5 |
| 2005/0064451 A1* | 3/2005 | Happe | C12Q 1/689 435/6.11 |
| 2013/0244238 A1* | 9/2013 | Neely | B82Y 25/00 435/6.11 |

* cited by examiner

[1]SEQ ID NO:6, [2]complementary sequence.
[4]SEQ ID NO:9, [3]complementary sequence.
[5]SEQ ID NO:43, [6]complementary sequence.
[7]SEQ ID NO:22, [8]complementary sequence.
[9]SEQ ID NO:23, [10]complementary sequence.
[11]SEQ ID NO:44, [12]complementary sequence.
[13]SEQ ID NO:45, [14]complementary sequence.

ent invention, the present invention provides a class of
ARTIFICIAL EXOGENOUS REFERENCE MOLECULE FOR TYPE AND ABUNDANCE COMPARISON AMONG DIFFERENT SPECIES OF MICROORGANISMS

TECHNICAL FIELD

The present invention relates to the technical field of microbial detection and analysis, and particularly to a class of artificial exogenous reference molecules for type and abundance comparison among different species of microorganisms.

BACKGROUND OF THE INVENTION

Microorganisms have many types involving viruses, bacteria, fungi and the like, and are ubiquitous in that a large number of microorganisms are present in the environment, surface of human body, surface of various cavities inside the human body and even within organs. Microorganisms can be divided into harmful microorganisms and beneficial microorganisms in terms of human health. Infection with microorganisms will mostly lead to a disease under a certain condition, but some beneficial microorganisms are requisite factors for maintaining health balance of the human body. With the advances in studies on life sciences, researchers have found that microorganisms that are mixed and concomitantly living in colonies at specific sites in the human body have relatively stable types in a certain proportion. Changes in the types and relative abundance among microorganisms may influence human health, and in certain cases are even main pathogenic factors. At the same time, the interactions present among microorganisms are not limited to interactions of microorganisms of the same species. More and more research results indicate that interactions are also present between different species of microorganisms, for example, between bacteria and viruses, between bacteria and fungi, between viruses and fungi, etc. Under some conditions, the interaction is just the reason causing the occurrence of diseases. Therefore, in recent years, scientists are paying increasing attentions to the system study taking microbial populations as one interactional organism, which is known by the name of Microbiome Study (Microbiom).

Prior to the appearance of large-scale sequencing techniques, the identification and classification among microorganisms mainly depend on traditional morphological, phenotypic, physiologic and biochemical classification, and these techniques have difficulty in large-scale batch detection, and are time-consuming, energy-consuming, and inaccurate in typing and quantification. With the rapid development of molecular biology, the current large-scale sequencing resolves this problem very well. A principle of the large-scale sequencing is achieved mainly based on features of genetic sequences of microorganisms.

Genetic sequences of the same species of microorganisms not only have conserved sequence regions that are essentially not varied or varied to a very low degree during evolution, but also have variable sequence regions expressed differentially among types. In nucleated organisms, ribosomal RNA (rRNA) and the corresponding encoding gene ribosomal DNA (rDNA) become very good regions, at the same time comprise two sequence regions and have appropriate length and size, so that they are suitable for sequence analysis under the frame of the prior art. At present, sequences of regions such as 5SrRNA/rDNA, 5.8SrRNA/rDNA, 16SrRNA/rDNA, 18SrRNA/rDNA, 23SrRNA/rDNA, and ITS (Internal transcribed space) are used more frequently. A particular principle consists in that universal primers are designed according to these conserved regions, thereby to obtain, by amplification, fragments of all the microorganisms of the same species in the sample collected, these fragments are sequenced to detect genetic sequences of a variable region between the two conserved universal primers, and difference of the sequences of these variable regions are analyzed so as to achieve classification of the microorganisms. The relative abundance among microorganisms can be known by detecting sequencing reads of different types of microorganisms.

The differences in genetic sequences among different species of microorganisms are relatively great, and conserved regions and sequences thereof for the sequencing detection are also frequently different. Different lengths of genetic sequences and amplified fragments are conditions restricting the amplification reaction. Therefore, at present, it is a relatively common practice to design an amplification kit, for the same species of microorganisms with the same universal primer, to carry out amplification and sequencing detection. Microorganisms with different universal primers are each amplified and sequenced separately, but amplification reactions and sequencing at different batches suffer from differences in amplification efficiency and other influencing factors across different batches. Thus the type and abundance detection of microorganisms can only be carried out in the same species, and at the same time the comparison cannot be carried out among different species of microorganisms colonized in the same spatial region.

SUMMARY OF THE INVENTION

Directing towards the above problem, the present invention provides a class of artificial exogenous reference molecules. The sequence may simultaneously contain universal primer sequence regions of two or more different microorganisms, also contains an artificially recognizable specific sequence, and is used for type and abundance comparison among different species of microorganisms.

In order to achieve the above objective according to the present invention, the present invention provides a class of artificial exogenous reference molecules for type and abundance comparison among different species of microorganisms. The artificial exogenous reference molecule includes several species detection regions and several linker sequence regions, where the species detection regions and the linker sequence regions are arranged alternately; at least two species detection regions are provided and are species detection regions for different species; and the linker sequence regions are random sequences different from the species sequence to be detected.

The species detection region includes a primer sequence region and a specific recognition region, where a primer sequence region located upstream of the specific recognition region is an upstream primer sequence region, and a primer sequence region located downstream of the specific recognition region is a downstream primer sequence region.

The primer sequence region has a sequence as shown in the Sequence Listing, and primer sequences in the Sequence Listing are all written from the 5' end to the 3' end.

The specific recognition region is a group of artificially designed and synthesized sequences, the arrangement information of the sequences is clearly known by the designer, and the sequence length simulates the characteristic detection sequence length of the corresponding species to be detected. The sequence of the specific recognition region has obviously specific difference from the DNA sequence of a genome in the species to be detected without homology The number of the species detection regions can be increased, and positions of the species detection regions for different species can be exchanged mutually. The species of the species detection region may also be replaced as required.

The present invention further provides a method for preparing the artificial exogenous reference molecule for type and abundance comparison among different species of microorganisms, with particular steps as follows.

Step 1: representative upstream and downstream primer sequences are selected from various regions attached in the Sequence Listing, an AGCT base sequence randomly arranged is designed between the upstream and downstream sequences, and the length of the fragment obtained comprising the upstream and downstream primers is an average length of the sequence of the species to be detected, to simulate the sequence of the species to be detected. However, the arrangement combination of the sequences thereof should not be homologous with the sequence of the species to be detected except the upstream and downstream primers.

Step 2: a linker sequence region is designed after the fragment, and the linker sequence region may be a sequence fragment of any length and is characterized by being not homologous with the sequence of the species to be detected.

Step 3: another group of representative upstream and downstream primer sequences are selected from various regions attached in the Sequence Listing again according to the method in the above Steps 1 and 2, a sequence fragment is designed between the upstream and downstream sequences, and the fragment should not be homologous with sequences in other parts of the artificial exogenous reference molecule.

Step 4: according to the designed sequences, full sequence synthesis is carried out employing a long fragment DNA synthetic method, in which a nucleotide AGCT of the synthetic gene is used as a raw material, to synthesize an oligonucleotide chain by employing a phosphoramidite method, and the fragments of the oligonucleotide chain are further linked and assembled by employing a full fragment enzymatic linking method or an enzymatic filling method, so as to obtain the whole artificial exogenous reference molecule that is designed.

A method for using the artificial exogenous reference molecule for type and abundance comparison among different species of microorganisms according to the present invention has particular steps as follows.

Step 1: the artificial exogenous reference molecule is synthesized, nucleic acid of the sample to be detected is purified and extracted, and a known amount of the exogenous reference molecule is added into the nucleic acid of the sample to be detected.

Step 2: after intensively and uniformly mixed, the mixture is equally divided into corresponding parts according to the quantity of the species requiring the detection, and each part is subjected to PCR amplification respectively using a kit, followed by subsequent sequencing, enzyme digestion or other DNA sequence analysis.

Step 3: relative amounts of various types of microorganisms with respect to the artificial exogenous reference molecule are obtained based on the detected amount of the artificial exogenous reference molecule, from results of quantitative or relative quantitative analysis of each species, and subjected to data normalization.

Step 4: the standardized data among species can be further compared with each other, so as to obtain data of relative type and abundance among the species.

The present invention has the beneficial effects as follows, as compared with the prior art.

The artificial exogenous reference molecule for type and abundance comparison among different species of microorganisms provided by the present invention is an artificially synthesized sequence, which may simultaneously contain the universal primer sequence regions of two or more different species of microorganisms, and also contains an artificially recognizable specific sequence. This artificially synthesized exogenous genic molecule fragment is added into a nucleic acid sample of the sample in a know and specific amount, and the mixture is divided into corresponding parts according to the quantity of the species requiring the detection. Each of the parts is subjected to subsequent specific amplification respectively. The artificial exogenous reference molecule can be amplified in a kit of each different species, and participates in the type and relative abundance comparison among different species of microorganisms in each amplification reaction. Relative abundance among different species of microorganism can be further compared, with the amount of this artificial exogenous reference molecule detected as a reference.

DETAILED DESCRIPTION OF THE PREFERRED

The present invention will be further set forth in detail below in conjunction with particular examples.

Example 1

Figure 1:
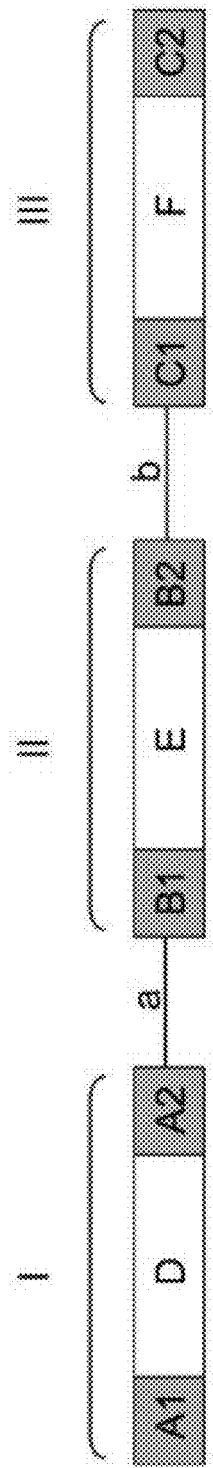
FIG. 1 is a structural representation of an artificial exogenous reference molecule for type and abundance comparison among different species of microorganisms according to the present invention.

Referring to FIG. 1, the present invention provides a class of artificial exogenous reference molecules for type and abundance comparison among different species of microorganisms. The artificial exogenous reference molecule includes several species detection regions and several linker sequence regions arranged alternately. Three species detection regions are provided, and are different species detection regions, i.e., the first species detection region I, the second species detection region II, and the third species detection region III, respectively. A linker sequence region located between the first species detection region I and the second species detection region II is the first linker sequence region a, a linker sequence region between the second species detection region II and the third species detection region III is the second linker sequence region b, and the first linker sequence region a and the second linker sequence region b are random sequences different from the species sequence to be detected.

The first species detection region I includes 16S rDNA primer sequence regions and the first specific recognition region D. A 16S rDNA upstream primer sequence region A1 is located upstream of the first specific recognition region D, and a 16S rDNA downstream primer sequence region A2 is located downstream of the first specific recognition region D.

The second species detection region II includes 18S rDNA primer sequence regions and the second specific recognition region E. An 18S rDNA upstream primer sequence region B1 is located upstream of the second specific recognition region E, and an 18S rDNA downstream primer sequence region B2 is located downstream of the second specific recognition region E.

The third species detection region III is a backup expansion region, and includes primer sequence regions for those except bacteria and fungi, and the third specific recognition region F. An upstream primer sequence region C1 for those except bacteria and fungi is located upstream of the third specific recognition region F, and a downstream primer sequence region C2 for those except bacteria and fungi is located downstream of the third specific recognition region F.

The 16S rDNA primer sequence regions, the 18S rDNA primer sequence regions and the primer sequence regions for those except bacteria and fungi have sequences as shown in the Sequence Listing.

The first specific recognition region D, the second specific recognition region E and the third specific recognition region F are respectively a group of artificially designed and synthesized sequences, the arrangement information of the sequences is clearly known by the designer, and the sequence length simulates the characteristic detection sequence length of the corresponding species to be detected. In particular, the 16S rDNA comprises about 1500 nucleotides and is divided into several variable sections of about 300 bp each; and the 18S rDNA comprises about 1900 nucleotides and likewise can be divided into several variable sections of about 300 bp each. The sequences the first specific recognition region D, the second specific recognition region E and the third specific recognition region F have obviously specific difference from the DNA sequence of a genome in the species to be detected without homology.

A method for preparing the artificial exogenous reference molecule for type and abundance comparison among different species of microorganisms according to the present invention has particular steps as follows.

Step 1: representative upstream and downstream primer sequences are selected from various regions attached in the Sequence Listing, an AGCT base sequence randomly arranged is designed between the upstream and downstream sequences, and the length of the fragment obtained comprising the upstream and downstream primers is an average length of the sequence of the species to be detected, to simulate the sequence of the species to be detected. However, the arrangement combination of the sequences thereof should not be homologous with the sequence of the species to be detected except the upstream and downstream primers.

Step 2: a linker sequence region is designed after the fragment, and the linker sequence region may be a sequence fragment of any length and is characterized by being not homologous with the sequence of the species to be detected.

Step 3: another group of representative upstream and downstream primer sequences are selected from various regions attached in the Sequence Listing again according to the method in the above Steps 1 and 2, a sequence fragment is designed between the upstream and downstream sequences, and the fragment should not be homologous with sequences in other parts of the artificial exogenous reference molecule.

Step 4: according to the designed sequences, full sequence synthesis is carried out employing a long fragment DNA synthetic method, in which a nucleotide AGCT of the synthetic gene is used as a raw material, to synthesize an oligonucleotide chain by employing a phosphoramidite method, and the fragments of the oligonucleotide chain are further linked and assembled by employing a full fragment enzymatic linking method or an enzymatic filling method, so as to obtain the whole artificial exogenous reference molecule that is designed.

There are many preparation and synthesis methods existing, and the preparation method is not limited to the above preparation method. Any method capable of preparing the artificial exogenous reference molecule according to the present inventors can be used.

A method for using the artificial exogenous reference molecule for type and abundance comparison among different species of microorganisms in the present invention has particular steps as follows.

Step 1: the artificial exogenous reference molecule is prepared and synthesized, nucleic acid of the sample to be detected is purified and extracted by employing an existing DNA purification kit, and a known amount of the exogenous reference molecule (for example 5 nM, so long as the exact amount is known) is added into the nucleic acid of the sample to be detected.

Step 2: after intensively and uniformly mixed, the mixture is equally divided into corresponding parts according to the quantity of the species requiring the detection, and each part is subjected to PCR amplification respectively using a specialized kit (an existing commercial reagent) according to each fixed reaction steps, followed by subsequent sequencing, and site analysis of enzyme digestion sequences. The artificial exogenous reference molecule can be amplified in a kit of each part of different species, and participates in the type and relative abundance comparison among different species of microorganisms in each amplification reaction.

Step 3: relative amounts of various types of microorganisms with respect to the artificial exogenous reference molecule are obtained based on the detected amount of the artificial exogenous reference molecule, from results of quantitative or relative quantitative analysis of each species, and subjected to data normalization.

Step 4: the standardized data among species can be further compared with each other, so as to obtain data of relative type and abundance among the species.

Bacteria and fungi are two general classes of common microorganisms, and have evolutionally relatively identical conserved sequences. Relative to bacteria and fungi, viral sequences have more complex types, comprising RNA viruses and DNA viruses. In the same species of viruses, some have a similar structure of conserved region—variable region—conserved region like bacteria and fungi, and some do not have such a highly conserved sequence. Using the artificial exogenous reference molecule designed according to the present invention, the former viral sample having a structure of an ideal genetic constitution can be detected for viral hypotype and abundance using large-scale sequencing like the detection of type and abundance of bacteria and fungi, whereas the latter does not has the ideal structure and thus can only be detected for relative abundance of a specific type of virus. In addition to HEV (Human EnteroVirus) in the Sequence Listing, other viruses such as HPV (Human PapillomaVirus) and herpes simplex virus can all be subjected to corresponding designs and applications.

Primer sequences in the Sequence Listing are all written from the 5' end to the 3' end. IUB standard codes are used in the mixed degenerate bases, where M=C:A, Y=C:T, K=G:T, R=A:G, S=G:C, W=A:T, I:hypoxanthine base. The mixing ratio is adjusted depending on specific circumstances.

Example 2

An artificial exogenous reference molecule for type and abundance comparison among different species of microorganisms provided in this examples is different from that in Example 1 in that, the primer sequence regions in the second species detection region II are replaced with ITS region rDNA primer sequence regions according to a recognition region well known in the art, an ITS region rDNA upstream primer sequence region B1 is located upstream of the second specific recognition region E, and an ITS region rDNA downstream primer sequence region B2 is located downstream of the second specific recognition region E; the second specific recognition region E is a group of artificially designed and synthesized sequences, and the arrangement information of the sequences is clearly known by the designer; the sequence length simulates the characteristic detection sequence length of the corresponding species to be detected, and in particular the ITS regions have a size of about 300 nucleotides. The rest is completely the same as that in Example 1.

Example 3

Figure 2:
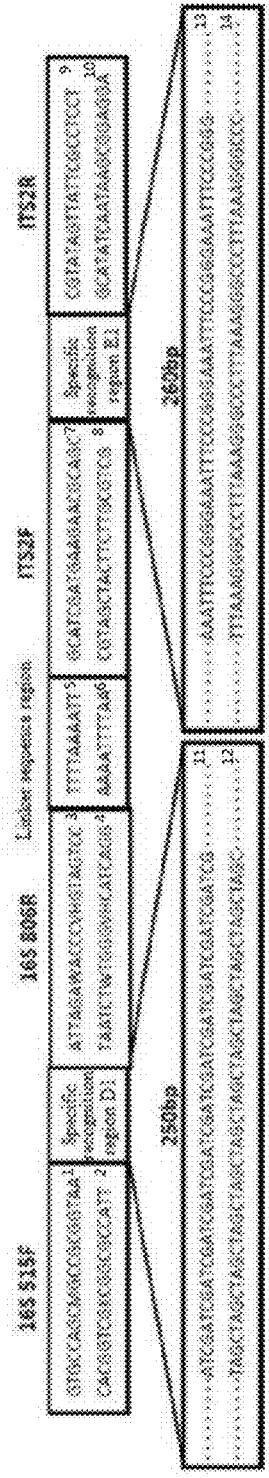
FIG. 2 is a structural representation of an artificial exogenous reference molecule for type and abundance comparison between bacteria and fungi in Example 3 according to the present invention.

In order to analyze the relative ratio of bacteria to fungi in the same sample, the exogenous reference molecule sequence as shown in FIG. 2 was artificially synthesized, and . . . in FIG. 2 means random sequences. The linker sequence region in the sequence of the artificial exogenous reference molecule is provided with, on the left side, a species detection region for detecting bacteria, and the primer sequence regions thereof simulate the forward and reverse primers of the 16S V4 region of the bacteria, where the upstream primer sequence region has a sequence as shown in SEQ ID NO: 6, and the downstream primer sequence region has a sequence as shown in SEQ ID NO: 9. A gene fragment with a sequence length of about 300 bp that simulates the fourth variable region of the bacteria has a specific recognition region D1 in the middle which is an artificially arranged specific sequence for recognizing the number of the exogenous fragments blended therein. The linker sequence region is provided with, on the right side, a species detection region for detecting fungi, and the primer sequence regions thereof simulate the forward and reverse primers of the second ITS region of the fungi, where the upstream primer sequence region has a sequence as shown in SEQ ID NO: 22, and the downstream primer sequence region has a sequence as shown in SEQ ID NO: 23. A gene fragment with a sequence length of about 300 bp that simulates the fourth variable region has a specific recognition region E1 in the middle. The sequences of the specific recognition region D1 and the specific recognition region E1 have obviously specific difference from the DNA sequence of a genome in the sample to be detected without homology.

Figure 3:
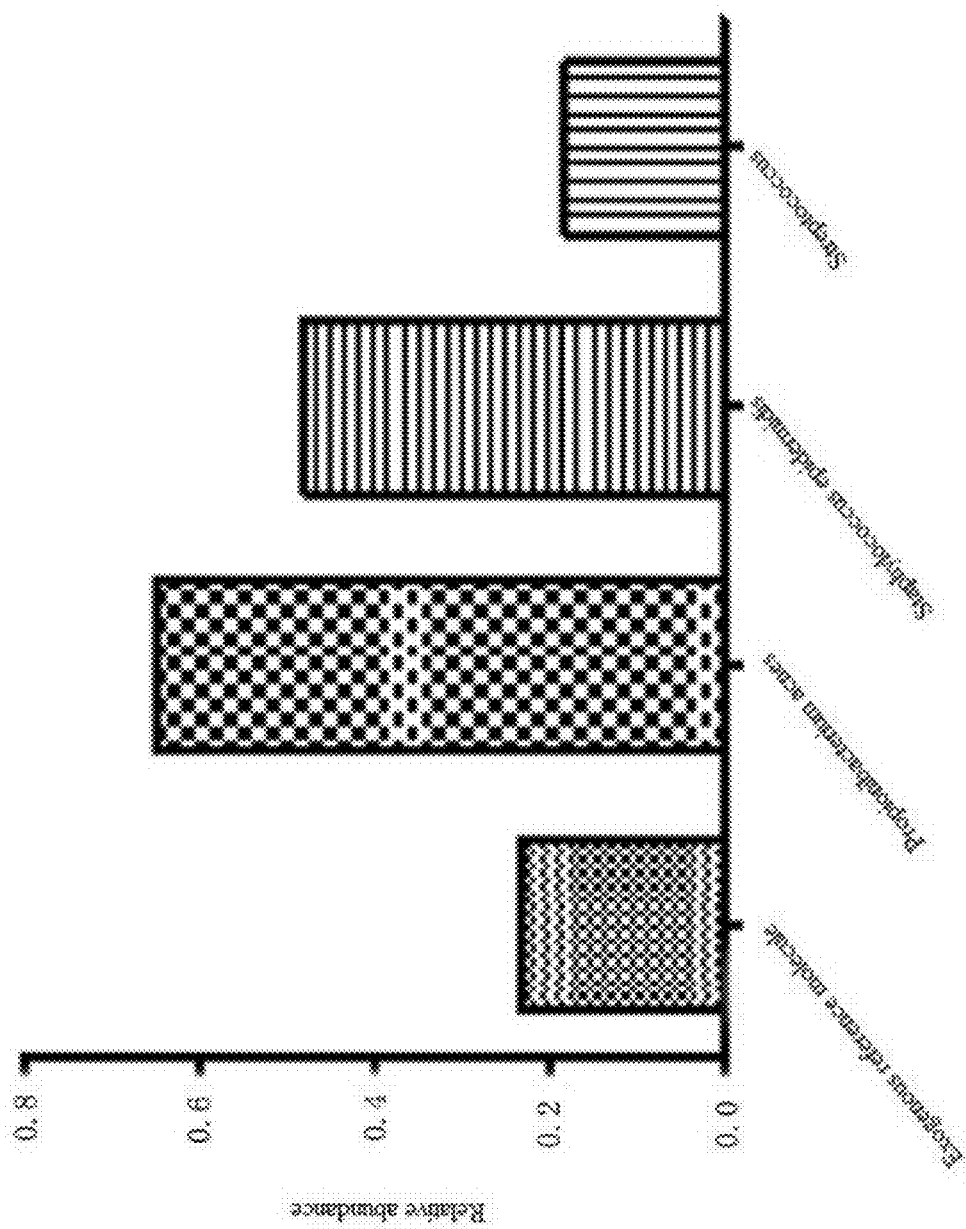
FIG. 3 is a detection result of type and relative abundance of bacteria in Example 3 according to the present invention.
Figure 4:
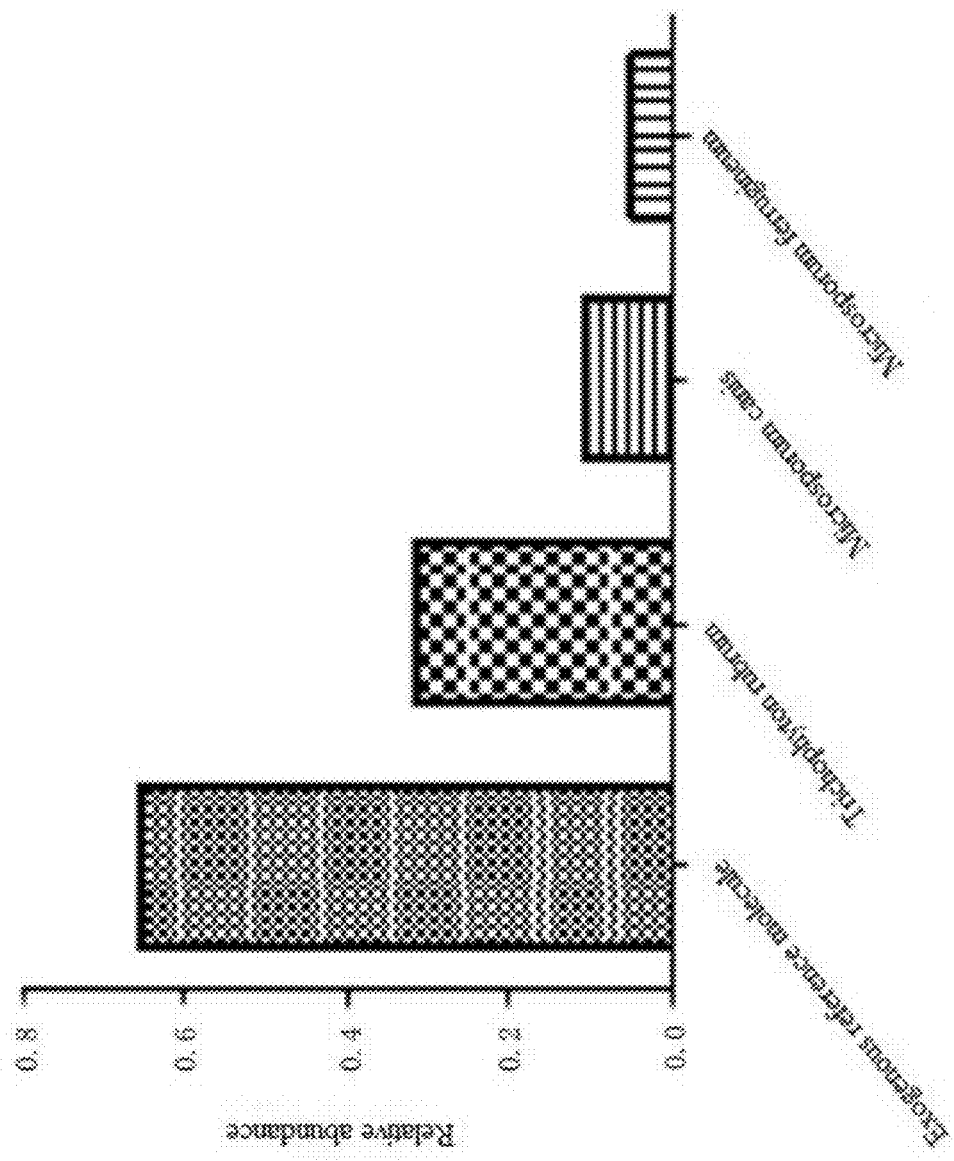
FIG. 4 is a detection result of type and relative abundance of fungi in Example 3 according to the present invention.
Figure 5:
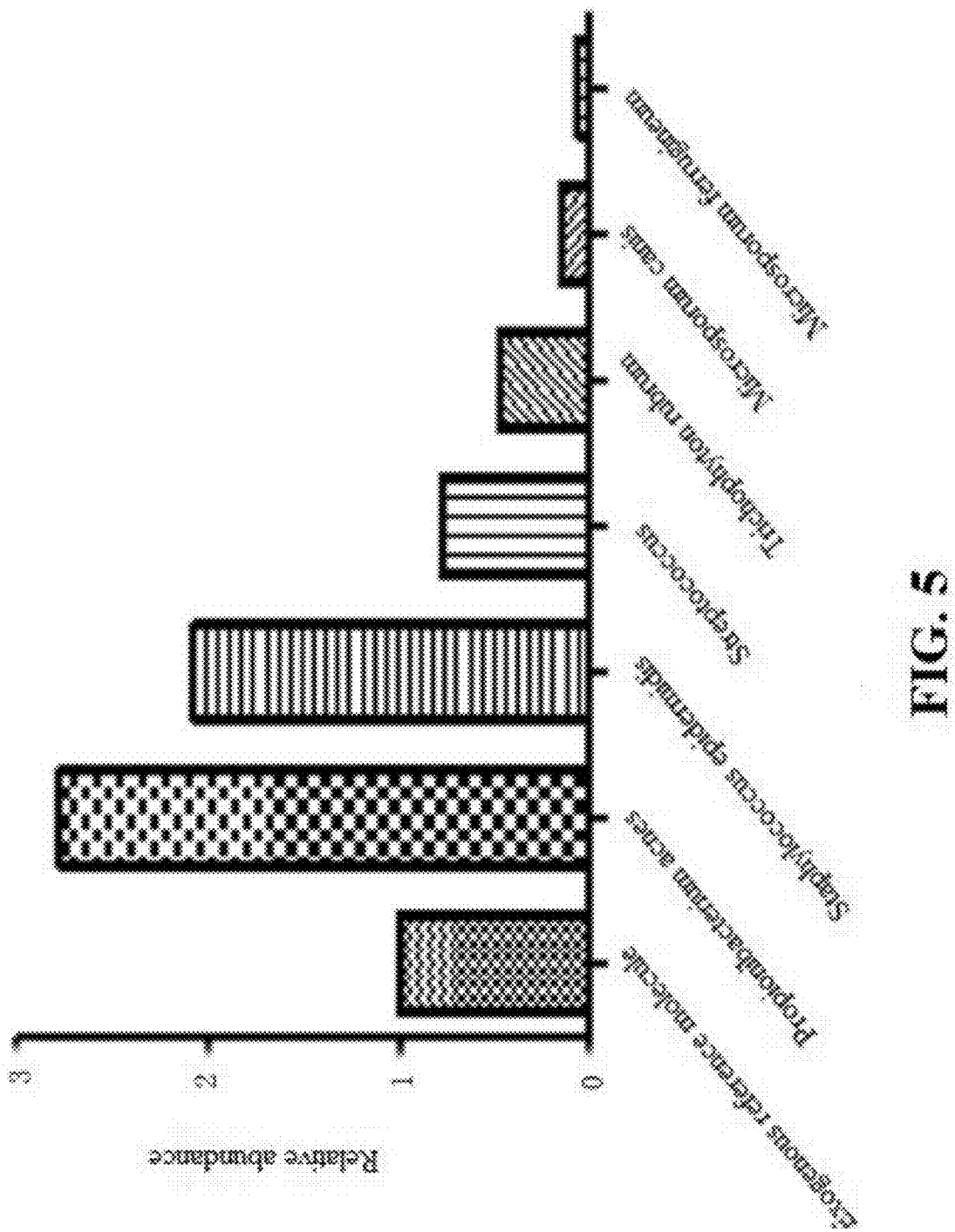
FIG. 5 is a detection result after data normalization in Example 3 according to the present invention.

An equal or a known amount of the artificial exogenous reference molecule is added into each reaction. After each amplification thereof followed by the participation in the comparison of type and relative abundance in each amplification reaction, relative amounts of various microorganisms with respect to the artificial exogenous reference molecule were obtained, with results as shown in FIGS. 3 and 4. Data normalization was carried out all based on the exogenous reference molecule, to be able to compare the different species of species with each other, with results as shown in FIG. 5. Therefore, the problems that, different species of microorganisms cannot be amplified using the same universal primer, the molecular biological reaction and the subsequent analysis must be carried out separately, and data of the relative abundance or interaction among the species cannot be obtained, are solved effectively.

Other various corresponding changes and variations can be made to the above by those of ordinary skill in the art according to technical solutions and technical conceptions according to the present invention, and all of these changes and variations should belong to the protection scope of claims of the present invention.

The invention claimed is:

1. An artificial exogenous reference nucleic acid molecule for analysis of microorganism type and abundance comprising:
   two or more species detection regions, and
   linker regions in between each of the two or more species detection regions,
wherein each of the species detection regions further comprises:
   a central specific recognition region flanked by a pair of primer binding regions:
      said pair of primer binding regions further comprise:
         an upstream primer binding region on the 5' side of the central specific recognition regions, and
         a downstream primer binding region on the 3' side of the central specific recognition region,
wherein the linker regions' base sequence is non-homologous to a genome of each microorganism under analysis,
the central specific recognition region base sequence is non-homologous to a genome of each microorganism under analysis,
each primer binding region base sequence is homologous to a corresponding region of the genome of one of the microorganisms under analysis such that the same pair of primers will bind and enable polymerase chain reaction (PCR) amplification of both the specific recognition region and a corresponding region of the genome of one of the microorganisms under analysis, and
wherein the amplification product from the species detection region is not homologous to the genome of the microorganism under analysis except for the upstream and downstream primer binding regions.

2. The artificial exogenous reference nucleic acid molecule as defined in claim 1, further comprising:
   the distance between each pair of upstream and downstream primer regions is about the same as the distance between the corresponding regions of the genome of each microorganism under analysis so that the resulting PCR product from each specific recognition region will be about the same size as the PCR products from each corresponding region from each microorganism under analysis.

3. The artificial exogenous reference nucleic acid molecule as defined in claim 2, further comprising;
   wherein said distance between each pair of upstream and downstream primer regions is about 300 bp.

4. The artificial exogenous reference nucleic acid molecule as defined in claim 1, further comprising:
   the base sequences of each pair of primer regions and corresponding regions of the genome of the microorganism under analysis are contiguous nucleic acid sequences selected from the group consisting of:
      5S ribosomal nucleic acid sequences,
      5.8S ribosomal nucleic acid sequences,
      16S ribosomal nucleic acid sequences,
      18S ribosomal nucleic acid sequences,
      23S ribosomal nucleic acid sequences, and
      Internal Transcribed Space (ITS) ribosomal nucleic acid sequences.

5. The artificial exogenous reference nucleic acid molecule as defined in claim 1, further comprising:
   the analysis further comprises analysis of virus type and abundance.

6. The artificial exogenous reference nucleic acid molecule as defined in claim 5, further comprising:
   wherein said virus type is selected from the group consisting of: HEV (Human Entero Virus) and HPV (Human Papilloma Virus).

* * * * *

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: 16S 21F primer

<400> SEQUENCE: 1
ttccggttga tcctgccgga                                              20

<210> SEQ ID NO 2
<211> LENGTH: 20
<212> TYPE: DNA
<213> ORGANISM: Artificial Sequence
<220> FEATURE:
<223> OTHER INFORMATION: 16S 27F primer
<220> FEATURE:
<221> NAME/KEY: misc_feature
```

<222> LOCATION: (12)..(12)
<223> OTHER INFORMATION: m=a or c

<400> SEQUENCE: 2
agagtttgat cmtggctcag                                                    20

<210> SEQ ID NO 3
<211> LENGTH: 20
<212> TYPE: DNA
<213> ORGANISM: Artificial Sequence
<220> FEATURE:
<223> OTHER INFORMATION: 16S 342R primer
<220> FEATURE:
<221> NAME/KEY: misc_feature
<222> LOCATION: (8)..(8)
<223> OTHER INFORMATION: s=g or c

<400> SEQUENCE: 3
tcctacgsga ggcagcagct                                                    20

<210> SEQ ID NO 4
<211> LENGTH: 16
<212> TYPE: DNA
<213> ORGANISM: Artificial Sequence
<220> FEATURE:
<223> OTHER INFORMATION: 16S 342R primer
<220> FEATURE:
<221> NAME/KEY: misc_feature
<222> LOCATION: (8)..(8)
<223> OTHER INFORMATION: s=g or c
<220> FEATURE:
<221> NAME/KEY: misc_feature
<222> LOCATION: (9)..(9)
<223> OTHER INFORMATION: y=c or t

<400> SEQUENCE: 4
ctgctgcsyc ccgtag                                                        16

<210> SEQ ID NO 5
<211> LENGTH: 19
<212> TYPE: DNA
<213> ORGANISM: Artificial Sequence
<220> FEATURE:
<223> OTHER INFORMATION: 16S 357F primer

<400> SEQUENCE: 5
ctcctacggg aggcagcag                                                     19

<210> SEQ ID NO 6
<211> LENGTH: 19
<212> TYPE: DNA
<213> ORGANISM: Artificial Sequence
<220> FEATURE:
<223> OTHER INFORMATION: 16S 515F primer
<220> FEATURE:
<221> NAME/KEY: misc_feature
<222> LOCATION: (9)..(9)
<223> OTHER INFORMATION: m=a or c

<400> SEQUENCE: 6
gtgccagcmg ccgcggtaa                                                     19

<210> SEQ ID NO 7
<211> LENGTH: 18
<212> TYPE: DNA
<213> ORGANISM: Artificial Sequence
<220> FEATURE:
<223> OTHER INFORMATION: 16S 519R primer
<220> FEATURE:

```
<221> NAME/KEY: misc_feature
<222> LOCATION: (2)..(2)
<223> OTHER INFORMATION: w=a or t
<220> FEATURE:
<221> NAME/KEY: misc_feature
<222> LOCATION: (14)..(14)
<223> OTHER INFORMATION: k=g or t

<400> SEQUENCE: 7
gwattaccgc ggckgctg                                                 18

<210> SEQ ID NO 8
<211> LENGTH: 16
<212> TYPE: DNA
<213> ORGANISM: Artificial Sequence
<220> FEATURE:
<223> OTHER INFORMATION: 16S 530F primer
<220> FEATURE:
<221> NAME/KEY: misc_feature
<222> LOCATION: (9)..(9)
<223> OTHER INFORMATION: m=a or c

<400> SEQUENCE: 8
gtgccagcmg ccgcgg                                                   16

<210> SEQ ID NO 9
<211> LENGTH: 20
<212> TYPE: DNA
<213> ORGANISM: Artificial Sequence
<220> FEATURE:
<223> OTHER INFORMATION: 16S 806R primer
<220> FEATURE:
<221> NAME/KEY: misc_feature
<222> LOCATION: (8)..(8)
<223> OTHER INFORMATION: h=a or c or t
<220> FEATURE:
<221> NAME/KEY: misc_feature
<222> LOCATION: (9)..(9)
<223> OTHER INFORMATION: v=a or g or c
<220> FEATURE:
<221> NAME/KEY: misc_feature
<222> LOCATION: (14)..(14)
<223> OTHER INFORMATION: w=a or t

<400> SEQUENCE: 9
ggactachvg ggtwtctaat                                               20

<210> SEQ ID NO 10
<211> LENGTH: 20
<212> TYPE: DNA
<213> ORGANISM: Artificial Sequence
<220> FEATURE:
<223> OTHER INFORMATION: 16S 907R primer
<220> FEATURE:
<221> NAME/KEY: misc_feature
<222> LOCATION: (11)..(11)
<223> OTHER INFORMATION: m=a or c
<220> FEATURE:
<221> NAME/KEY: misc_feature
<222> LOCATION: (15)..(15)
<223> OTHER INFORMATION: r=g or a

<400> SEQUENCE: 10
ccgtcaattc mtttragttt                                               20

<210> SEQ ID NO 11
<211> LENGTH: 20
<212> TYPE: DNA
<213> ORGANISM: Artificial Sequence
<220> FEATURE:
<223> OTHER INFORMATION: 16S 926F primer
```

```
<220> FEATURE:
<221> NAME/KEY: misc_feature
<222> LOCATION: (6)..(6)
<223> OTHER INFORMATION: y=t or c
<220> FEATURE:
<221> NAME/KEY: misc_feature
<222> LOCATION: (10)..(10)
<223> OTHER INFORMATION: k=g or t

<400> SEQUENCE: 11
aaactyaaak gaattgacgg                                                  20

<210> SEQ ID NO 12
<211> LENGTH: 15
<212> TYPE: DNA
<213> ORGANISM: Artificial Sequence
<220> FEATURE:
<223> OTHER INFORMATION: 16S 1100R primer

<400> SEQUENCE: 12
gggttgcgct cgttg                                                       15

<210> SEQ ID NO 13
<211> LENGTH: 16
<212> TYPE: DNA
<213> ORGANISM: Artificial Sequence
<220> FEATURE:
<223> OTHER INFORMATION: 16S 1114F primer

<400> SEQUENCE: 13
gcaacgagcg caaccc                                                      16

<210> SEQ ID NO 14
<211> LENGTH: 22
<212> TYPE: DNA
<213> ORGANISM: Artificial Sequence
<220> FEATURE:
<223> OTHER INFORMATION: 16S 1492R primer
<220> FEATURE:
<221> NAME/KEY: misc_feature
<222> LOCATION: (6)..(6)
<223> OTHER INFORMATION: y=t or c

<400> SEQUENCE: 14
tacggytacc ttgttacgac tt                                               22

<210> SEQ ID NO 15
<211> LENGTH: 17
<212> TYPE: DNA
<213> ORGANISM: Artificial Sequence
<220> FEATURE:
<223> OTHER INFORMATION: 16S 1525R primer
<220> FEATURE:
<221> NAME/KEY: misc_feature
<222> LOCATION: (10)..(10)
<223> OTHER INFORMATION: w=a or t
<220> FEATURE:
<221> NAME/KEY: misc_feature
<222> LOCATION: (15)..(15)
<223> OTHER INFORMATION: r=g or a

<400> SEQUENCE: 15
aaggaggtgw tccarcc                                                     17

<210> SEQ ID NO 16
<211> LENGTH: 19
<212> TYPE: DNA
<213> ORGANISM: Artificial Sequence
<220> FEATURE:
```

```
<223> OTHER INFORMATION: 18S NS1 primer

<400> SEQUENCE: 16
gtagtcatat gcttgtctc                                                 19

<210> SEQ ID NO 17
<211> LENGTH: 20
<212> TYPE: DNA
<213> ORGANISM: Artificial Sequence
<220> FEATURE:
<223> OTHER INFORMATION: 18S NS4 primer

<400> SEQUENCE: 17
cttccgtcaa ttcctttaag                                                20

<210> SEQ ID NO 18
<211> LENGTH: 24
<212> TYPE: DNA
<213> ORGANISM: Artificial Sequence
<220> FEATURE:
<223> OTHER INFORMATION: 18S nu-SSU-0817 primer
<220> FEATURE:
<221> NAME/KEY: misc_feature
<222> LOCATION: (16)..(17)
<223> OTHER INFORMATION: r=g or a

<400> SEQUENCE: 18
ttagcatgga ataatrraat agga                                           24

<210> SEQ ID NO 19
<211> LENGTH: 20
<212> TYPE: DNA
<213> ORGANISM: Artificial Sequence
<220> FEATURE:
<223> OTHER INFORMATION: 18S nu-SSU-0817 primer
<220> FEATURE:
<221> NAME/KEY: misc_feature
<222> LOCATION: (11)..(11)
<223> OTHER INFORMATION: y=t or c; 18S nu-SSU-1536 primer

<400> SEQUENCE: 19
attgcaatgc yctatcccca                                                20

<210> SEQ ID NO 20
<211> LENGTH: 19
<212> TYPE: DNA
<213> ORGANISM: Artificial Sequence
<220> FEATURE:
<223> OTHER INFORMATION: 18S nu-SSU-1536 primer
<220> FEATURE:
<221> NAME/KEY: misc_feature
<222> LOCATION: (11)..(11)
<223> OTHER INFORMATION: y=t or c

<400> SEQUENCE: 20
tccgtaggtg aacctgcgg                                                 19

<210> SEQ ID NO 21
<211> LENGTH: 20
<212> TYPE: DNA
<213> ORGANISM: Artificial Sequence
<220> FEATURE:
<223> OTHER INFORMATION: ITS2 primer

<400> SEQUENCE: 21
gctgcgttct tcatcgatgc                                                20
```

```
<210> SEQ ID NO 22
<211> LENGTH: 20
<212> TYPE: DNA
<213> ORGANISM: Artificial Sequence
<220> FEATURE:
<223> OTHER INFORMATION: ITS2F primer

<400> SEQUENCE: 22
gcatcgatga agaacgcagc                                                 20

<210> SEQ ID NO 23
<211> LENGTH: 20
<212> TYPE: DNA
<213> ORGANISM: Artificial Sequence
<220> FEATURE:
<223> OTHER INFORMATION: ITS2R primer

<400> SEQUENCE: 23
tcctccgctt attgatatgc                                                 20

<210> SEQ ID NO 24
<211> LENGTH: 18
<212> TYPE: DNA
<213> ORGANISM: Artificial Sequence
<220> FEATURE:
<223> OTHER INFORMATION: ITS5 primer

<400> SEQUENCE: 24
ggaaggtaaa agtcaagg                                                   18

<210> SEQ ID NO 25
<211> LENGTH: 23
<212> TYPE: DNA
<213> ORGANISM: Artificial Sequence
<220> FEATURE:
<223> OTHER INFORMATION: ITS12F primer

<400> SEQUENCE: 25
cttggtcatt ttagaggaag taa                                             23

<210> SEQ ID NO 26
<211> LENGTH: 27
<212> TYPE: DNA
<213> ORGANISM: Artificial Sequence
<220> FEATURE:
<223> OTHER INFORMATION: ITS12R primer

<400> SEQUENCE: 26
tatggtctag ttctctagag gaagtaa                                         27

<210> SEQ ID NO 27
<211> LENGTH: 23
<212> TYPE: DNA
<213> ORGANISM: Artificial Sequence
<220> FEATURE:
<223> OTHER INFORMATION: ITS42F primer

<400> SEQUENCE: 27
caggagactt gtacacggtc cag                                             23

<210> SEQ ID NO 28
<211> LENGTH: 22
<212> TYPE: DNA
<213> ORGANISM: Artificial Sequence
<220> FEATURE:
<223> OTHER INFORMATION: ITS42R primer
```

```
<400> SEQUENCE: 28
cagacttgat actatggtcc ag                                              22

<210> SEQ ID NO 29
<211> LENGTH: 22
<212> TYPE: DNA
<213> ORGANISM: Artificial Sequence
<220> FEATURE:
<223> OTHER INFORMATION: ITS86 primer

<400> SEQUENCE: 29
gtgaatcatc gaatctttga ac                                              22

<210> SEQ ID NO 30
<211> LENGTH: 20
<212> TYPE: DNA
<213> ORGANISM: Artificial Sequence
<220> FEATURE:
<223> OTHER INFORMATION: 5S 26SF primer

<400> SEQUENCE: 30
atcctttgca gacgacttga                                                 20

<210> SEQ ID NO 31
<211> LENGTH: 20
<212> TYPE: DNA
<213> ORGANISM: Artificial Sequence
<220> FEATURE:
<223> OTHER INFORMATION: 5S 5SR primer

<400> SEQUENCE: 31
agcttgactt cgcagatcgg                                                 20

<210> SEQ ID NO 32
<211> LENGTH: 19
<212> TYPE: DNA
<213> ORGANISM: Artificial Sequence
<220> FEATURE:
<223> OTHER INFORMATION: 5S CNL12 primer

<400> SEQUENCE: 32
ctgaacgcct ctaagtcag                                                  19

<210> SEQ ID NO 33
<211> LENGTH: 21
<212> TYPE: DNA
<213> ORGANISM: Artificial Sequence
<220> FEATURE:
<223> OTHER INFORMATION: 5S CNS1 primer

<400> SEQUENCE: 33
gagacaagca tatgactact g                                               21

<210> SEQ ID NO 34
<211> LENGTH: 25
<212> TYPE: DNA
<213> ORGANISM: Artificial Sequence
<220> FEATURE:
<223> OTHER INFORMATION: HEV NTR EV1-446 primer

<400> SEQUENCE: 34
tccggcccct gaatgcggct aatcc                                           25

<210> SEQ ID NO 35
<211> LENGTH: 26
```

```
<212> TYPE: DNA
<213> ORGANISM: Artificial Sequence
<220> FEATURE:
<223> OTHER INFORMATION: HEV NTR EV2-559 primer

<400> SEQUENCE: 35
acacggacac ccaaagtagt cggtcc                                              26

<210> SEQ ID NO 36
<211> LENGTH: 20
<212> TYPE: DNA
<213> ORGANISM: Artificial Sequence
<220> FEATURE:
<223> OTHER INFORMATION: HEV NTR EV2-559 primer
<220> FEATURE:
<221> NAME/KEY: modified_base
<222> LOCATION: (3)..(3)
<223> OTHER INFORMATION: n = hypoxanthine base
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (6)..(6)
<223> OTHER INFORMATION: n = hypoxanthine base
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: y=t or c
<220> FEATURE:
<221> NAME/KEY: misc_feature
<222> LOCATION: (12)..(12)
<223> OTHER INFORMATION: n = hypoxanthine base
<220> FEATURE:
<221> NAME/KEY: misc_feature
<222> LOCATION: (15)..(15)
<223> OTHER INFORMATION: n = hypoxanthine base
<220> FEATURE:
<221> NAME/KEY: misc_feature
<222> LOCATION: (18)..(18)
<223> OTHER INFORMATION: r=g or a

<400> SEQUENCE: 36
gcnccngayt gntgnccraa                                                     20

<210> SEQ ID NO 37
<211> LENGTH: 20
<212> TYPE: DNA
<213> ORGANISM: Artificial Sequence
<220> FEATURE:
<223> OTHER INFORMATION: HEV 2A and VP1 P2-2951 primers
<220> FEATURE:
<221> NAME/KEY: misc_feature
<222> LOCATION: (6)..(6)
<223> OTHER INFORMATION: y=t or c
<220> FEATURE:
<221> NAME/KEY: modified_base
<222> LOCATION: (9)..(9)
<223> OTHER INFORMATION: n = hypoxanthine base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (12)..(12)
<223> OTHER INFORMATION: n = hypoxanthine base
<220> FEATURE:
<221> NAME/KEY: misc_feature
<222> LOCATION: (12)..(12)
```

```
<223> OTHER INFORMATION: n is a, c, g, or t
<220> FEATURE:
<221> NAME/KEY: modified_base
<222> LOCATION: (15)..(15)
<223> OTHER INFORMATION: n = hypoxanthine base
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: n = hypoxanthine base
<220> FEATURE:
<221> NAME/KEY: misc_feature
<222> LOCATION: (18)..(18)
<223> OTHER INFORMATION: n is a, c, g, or t

<400> SEQUENCE: 37
atgtaygtnc cnccnggngg                                                  20

<210> SEQ ID NO 38
<211> LENGTH: 20
<212> TYPE: DNA
<213> ORGANISM: Artificial Sequence
<220> FEATURE:
<223> OTHER INFORMATION: HEV 2A and VP1 P3-2951 primers
<220> FEATURE:
<221> NAME/KEY: misc_feature
<222> LOCATION: (6)..(6)
<223> OTHER INFORMATION: y=t or c
<220> FEATURE:
<221> NAME/KEY: misc_feature
<222> LOCATION: (7)..(7)
<223> OTHER INFORMATION: r=g or a
<220> FEATURE:
<221> NAME/KEY: modified_base
<222> LOCATION: (9)..(9)
<223> OTHER INFORMATION: n = hypoxanthine base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (12)..(12)
<223> OTHER INFORMATION: n = hypoxanthine base
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: m=a or c
<220> FEATURE:
<221> NAME/KEY: misc_feature
<222> LOCATION: (15)..(15)
<223> OTHER INFORMATION: n = hypoxanthine base
<220> FEATURE:
<221> NAME/KEY: misc_feature
<222> LOCATION: (18)..(18)
<223> OTHER INFORMATION: n = hypoxanthine base

<400> SEQUENCE: 38
atgtayrtnc cnmcnggngc                                                  20

<210> SEQ ID NO 39
<211> LENGTH: 20
<212> TYPE: DNA
<213> ORGANISM: Hepatitis virus
<220> FEATURE:
<221> NAME/KEY: modified_base
<222> LOCATION: (3)..(6)
<223> OTHER INFORMATION: i; HEV 2A and VP1 P4-2612 primers
```

```
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: y=t or c; HEV 2A and VP1 P4-2612 primers
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: r=g or a; HEV 2A and VP1 P4-2612 primers
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n=a or g or c or t, HEV 2A and VP1 P4-2612
     primers

<400> SEQUENCE: 39
acngcngyng aracnggnca                                                  20

<210> SEQ ID NO 40
<211> LENGTH: 19
<212> TYPE: DNA
<213> ORGANISM: Artificial Sequence
<220> FEATURE:
<223> OTHER INFORMATION: HEV 2A and VP1 P5-2612 primers
<220> FEATURE:
<221> NAME/KEY: modified_base
<222> LOCATION: (3)..(3)
<223> OTHER INFORMATION: n = hypoxanthine base
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (6)..(6)
<223> OTHER INFORMATION: n = hypoxanthine base
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: n = hypoxanthine base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: r=g or a
<220> FEATURE:
<221> NAME/KEY: misc_feature
<222> LOCATION: (15)..(15)
<223> OTHER INFORMATION: n = hypoxanthine base
<220> FEATURE:
<221> NAME/KEY: misc_feature
<222> LOCATION: (18)..(18)
<223> OTHER INFORMATION: n=a or g or c or t

<400> SEQUENCE: 40
```
acngcngtng aracnggng                                                    19

<210> SEQ ID NO 41
<211> LENGTH: 20
<212> TYPE: DNA
<213> ORGANISM: Artificial Sequence
<220> FEATURE:
<223> OTHER INFORMATION: HEV 2A and VP1 P6-2612 primers
<220> FEATURE:
<221> NAME/KEY: misc_feature
<222> LOCATION: (3)..(3)
<223> OTHER INFORMATION: r=g or a
<220> FEATURE:
<221> NAME/KEY: modified_base
<222> LOCATION: (6)..(6)
<223> OTHER INFORMATION: n = hypoxanthine base
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: n = hypoxanthine base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (12)..(12)
<223> OTHER INFORMATION: r=g or a
<220> FEATURE:
<221> NAME/KEY: modified_base
<222> LOCATION: (15)..(15)
<223> OTHER INFORMATION: n = hypoxanthine base
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n=a or g or c or t

<400> SEQUENCE: 41
cargcngcng aracnggngc                                                   20

<210> SEQ ID NO 42
<211> LENGTH: 19
<212> TYPE: DNA
<213> ORGANISM: Artificial Sequence
<220> FEATURE:
<223> OTHER INFORMATION: HEV 2A and VP1 P7-2969 primers
<220> FEATURE:
<221> NAME/KEY: modified_base
<222> LOCATION: (2)..(2)
<223> OTHER INFORMATION: n = hypoxanthine base
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (5)..(5)
<223> OTHER INFORMATION: n = hypoxanthine base
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (8)..(8)
<223> OTHER INFORMATION: n = hypoxanthine base
<220> FEATURE:

```
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (11)..(11)
<223> OTHER INFORMATION: n = hypoxanthine base
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: y=t or c
<220> FEATURE:
<221> NAME/KEY: misc_feature
<222> LOCATION: (14)..(14)
<223> OTHER INFORMATION: r=g or a
<220> FEATURE:
<221> NAME/KEY: misc_feature
<222> LOCATION: (15)..(15)
<223> OTHER INFORMATION: w=a or t

<400> SEQUENCE: 42
cnccnggngg nayrwacat                                              19
```